US012596845B2

(12) United States Patent
Hughes

(10) Patent No.: US 12,596,845 B2
(45) Date of Patent: Apr. 7, 2026

(54) SECURE ULTRASOUND SYSTEM

(71) Applicant: Novosound Ltd., Newhouse (GB)

(72) Inventor: David Hughes, Newhouse (GB)

(73) Assignee: Novosound Ltd., Newhouse (GB)

( * ) Notice: Subject to any disclaimer, the term of this patent is extended or adjusted under 35 U.S.C. 154(b) by 69 days.

(21) Appl. No.: 17/920,745

(22) PCT Filed: Apr. 23, 2021

(86) PCT No.: PCT/GB2021/050996
§ 371 (c)(1),
(2) Date: Oct. 21, 2022

(87) PCT Pub. No.: WO2021/214490
PCT Pub. Date: Oct. 28, 2021

(65) Prior Publication Data
US 2023/0177217 A1     Jun. 8, 2023

(30) Foreign Application Priority Data

Apr. 24, 2020     (GB) ..................................... 2006048

(51) Int. Cl.
G06F 21/64     (2013.01)
A61B 8/00     (2006.01)
H04L 9/00     (2022.01)
(52) U.S. Cl.
CPC ............ *G06F 21/64* (2013.01); *A61B 8/4227* (2013.01); *A61B 8/565* (2013.01); *H04L 9/50* (2022.05)
(58) Field of Classification Search
CPC . G06F 21/64; H04L 9/50; A61B 8/565; A61B 8/46; A61B 8/52; A61B 8/5207–5223; A61B 8/543
See application file for complete search history.

(56) References Cited

U.S. PATENT DOCUMENTS 4,202,215 A * 5/1980 Meyer ................ G01N 29/4454
73/599
5,572,060 A * 11/1996 Butler ................... H01L 31/032
257/E27.008
(Continued)

FOREIGN PATENT DOCUMENTS

CN          103235039 A     8/2013
JP          2010192060 A     9/2010
(Continued)

OTHER PUBLICATIONS

Leewayhertz, Apr. 24, 2019, "Blockchain and IoT—Bringing Transformation to the World", Hackernoon.com [online], Available from https://medium.com/hackernoon/blockchain-and-iotbringing-transformation-to-the-world-2169cb0c498a<https://protect-us.mimecast.com/s/-hKPCR6Kr0lvRM30t936Zf?domain=medium.com> [Accessed Jul. 27, 2022].
(Continued)

*Primary Examiner* — Oommen Jacob
(74) *Attorney, Agent, or Firm* — Patterson + Sheridan, LLP

(57)     ABSTRACT

An ultrasonic device comprising at least one ultrasonic transducer that is operable to receive an ultrasonic signal and produce an electrical signal responsive to, and indicative of, the received ultrasonic signal; an on-board processing system for processing the electrical signal to determine data therefrom; and a communications system for communicating the data with an external processing system, wherein the ultrasonic device is configured to protect the integrity of the ultrasonic data using a distributed ledger.

19 Claims, 6 Drawing Sheets

(56)                References Cited

U.S. PATENT DOCUMENTS

| | | | | |
|---|---|---|---|---|
| 2003/0062804 | A1* | 4/2003 | Uchiyama | H10N 30/073 |
| 2004/0152957 | A1 | 8/2004 | Stivoric et al. | |
| 2008/0001735 | A1 | 1/2008 | Tran | |
| 2008/0018199 | A1* | 1/2008 | Trolier-McKinstry | B06B 1/0629 |
| | | | | 310/311 |
| 2008/0091090 | A1 | 4/2008 | Guillory et al. | |
| 2012/0065479 | A1* | 3/2012 | Lahiji | A61B 8/4427 |
| | | | | 600/459 |
| 2012/0197118 | A1 | 8/2012 | Lisiecki et al. | |
| 2017/0173262 | A1* | 6/2017 | Veltz | G16H 20/17 |
| 2018/0001184 | A1* | 1/2018 | Tran | G16H 50/20 |
| 2018/0306609 | A1 | 10/2018 | Agarwal et al. | |
| 2019/0025280 | A1* | 1/2019 | Kaditz | G16H 50/50 |
| 2019/0042981 | A1* | 2/2019 | Bendfeldt | G16H 20/70 |
| 2019/0236389 | A1 | 8/2019 | Obaidi | |
| 2019/0283082 | A1 | 9/2019 | Hughes et al. | |
| 2019/0354693 | A1* | 11/2019 | Yoon | H04L 9/50 |
| 2020/0008299 | A1 | 1/2020 | Tran et al. | |
| 2020/0088602 | A1 | 3/2020 | Tran et al. | |
| 2020/0097951 | A1* | 3/2020 | Abramson | G06Q 30/0207 |
| 2020/0358782 | A1* | 11/2020 | Hager | G06F 21/645 |
| 2023/0177217 | A1* | 6/2023 | Hughes | A61B 8/565 |
| | | | | 600/459 |

FOREIGN PATENT DOCUMENTS

| | | | |
|---|---|---|---|
| KR | 101875725 | B1 | 7/2018 |
| WO | 02/19897 | A2 | 3/2002 |

OTHER PUBLICATIONS

Jen Clark, Dec. 14, 2017, "Cheat Sheet: What has blockchain to do with the IoT?" IBM.com [online] Available from https://www.ibm.com/blogs/internet-of-things/iot-and-blockchain-cheat-sheet/ <https://protect-us.mimecast.com/s/Jw35CVO2ykix5Wpkcz7cXx?domain=ibm.com> [Accessed Jul. 27, 2022].

Elena Serneniak, Sep. 26, 2019, "How can the Blockchain Secure IoT Networks?" Apriorit.com [online] Available from https://www.apriorit.com/dev-blog/638-blockchain-how-can-blockchain-secure-iot-networks <https://protect-us.mimecast.com/s/ib5lCW6Kzll5PMnXSKizsl?domain=apriorit.com> [Accessed Jul. 27, 2022].

Zhaohong Zhang "Matched-Filter Ultrasonic Sensing: Theory and Implementation" Dec. 2017, Texas Instruments.

GB Exam Report, GB Application No. 2006048.9 dated Mar. 22, 2022.

GB Exam Report, GB Application No. 2006048.9 dated Jul. 29, 2022.

International Search Report and Written Opinion for PCT/GB2021/050996 dated Jul. 6, 2021.

Search Report from GB2006048.9 dated Oct. 5, 2020.

International Preliminary Report on Patentability PCT/GB2021/050996 dated Nov. 3, 2022, consists of 7 pages.

Japan Office Action, JP Application No. 2022-564299 date Apr. 1, 2025.

Japan Office Action, JP Application No. 2022-564299 date Dec. 16, 2025.

* cited by examiner

15

SECURE ULTRASOUND SYSTEM

FIELD

The present disclosure relates to a secure ultrasound system that optionally utilizes a flexible, thin film piezoelectric ultrasound transducer array.

BACKGROUND

Ultrasound spans a range of sound frequencies that are higher than the range that can be heard by humans, and generally have frequencies of greater than 20 kHz. Typical ranges of operation extend from 100 kHz up to several Gigahertz. Due to the much higher frequencies involved, ultrasonic devices are typically very different from those generally used for audible applications.

Analysis using ultrasound waves shows great promise in a range of applications, particularly in imaging such as medical imaging but also in fields such as non-destructive testing (NDT), particularly in industrial NDT. However, whilst well used in hospitals and other controlled healthcare settings, ultrasound imaging systems have traditionally been overly expensive and complex for many applications.

Conventional ultrasonic transducers are generally formed from bulk ceramic materials, which can be high cost, bulky and difficult to manufacture, particularly with the shapes and properties desired for many applications. Traditional ceramic materials used in ultrasound are generally not suitable for very high temperature operation, making them unsuitable for some applications. In particular, the combination of being able to operate at high temperature and with sufficient resolution is problematic for many traditional ultrasound transducers. Furthermore, traditional ultrasound transducers are not easy to manufacture using automated techniques and often require a high degree of manual operation. Improved ultrasonic transducers and methods for manufacturing them are therefore desirable.

However, even if low cost ultrasonic arrays for mass-market applications could be produced, then data security from such devices may be an issue for some applications.

SUMMARY

Various aspects of the present invention are defined in the independent claims. Some preferred features are defined in the dependent claims.

According to a first example of the present disclosure is an ultrasonic device comprising:

at least one ultrasonic transducer that is operable to receive an ultrasonic signal and produce an electrical signal responsive to, and indicative of, the received ultrasonic signal;

an on-board processing system for processing the electrical signal to determine data therefrom; and a communications system for communicating the data with an external processing system.

The ultrasonic device may be configured for monitoring an entity. The ultrasonic device may be configured to collect ultrasonic measurements of the entity. The ultrasonic device may be configured to emit an emitted ultrasonic signal, e.g. from one or more of the at least one transducers, onto and/or into the entity. The received ultrasonic signal received by the at least one ultrasonic transducer may be formed from one or more reflections of the emitted ultrasonic signal from the entity. The ultrasonic device may be attached or attachable to the entity. The ultrasonic device may comprise one or more fixings, such as bands, straps, screw or bolt fittings, clamps and/or the like for attaching to the entity.

The ultrasonic device may be a wearable device. The entity may be a living entity, such as a human or an animal. The entity may be an organic or a biological entity. The one or more fixings of the ultrasonic device may be configured to attach the ultrasonic device to the living entity. The ultrasonic device may be configured to attach the living entity by fixing around the torso, chest, a limb, or mounted to a head or neck of the living entity, e.g. by using straps or bands or by being comprised in or affixed to a worn item. The ultrasonic device may be or comprise an imaging device, e.g. for imaging the entity.

The ultrasonic device may be a non-destructive testing device. The entity may be an inanimate object. The entity may be a structure, pipe, conduit, support, building or other piece of architecture, a bridge, a beam, a reinforcing member or the like, but is not limited to these. The entity may be inorganic. The entity may be formed or partially formed of metal, a composite material, concrete, a polymeric material and/or the like. For example, the entity may be a component of a vehicle, such as a panel, support, strut or member for an aeroplane, helicopter, drone or other flying vehicle; a car, truck, bus or other motor vehicle, a ship or boat or other form of vessel, a satellite, spacecraft, rocket or other space vehicle or entity, from amongst other possibilities. The monitored properties may comprise mechanical properties of the entity.

The ultrasonic device may comprise on-board data storage, such as solid-state memory or SSD, optical storage, a hard-drive or other magnetic storage device, Ram, ROM, or EEPROM or the like. The ultrasonic device may be configured to store the data determined from the received ultrasonic signal and/or the values of any parameters or metadata required to determine or process the data from the received ultrasonic signal.

The electrical signal produced by the ultrasonic transducer may represent properties of the ultrasonic signal, such as amplitude of the ultrasonic signal and/or the like at one or more or a continuum of times. The data determined by the on-board processing system may comprise data derived from the ultrasonic signal, such as time of flight, time since emission, attenuation, frequency, frequency shift, Doppler shift, and/or the like. The data determined by the on-board processing system may comprise data that represents a measure or value of a state, property, parameter or condition of the entity. The data determined by the on-board processing system may represent qualitative information, such as qualitative information that is indicative or provides a measure or value of a state, property, parameter or condition of the entity. The on-board processing system may be configured to store or at least temporarily the data and/or historical data, such as values and/or historical values of the state, property, parameter or condition of the entity, e.g. using the on-board data storage.

By way of non-exhaustive example, the data determined by the on-board processing system may comprise an indication or measure of a health or physiological condition such as pneumonia, chest infection, dehydration, muscle damage, skin damage, digestive health issues, cardiac dysfunction, or other suitable health, dental or physiological condition or complaint. In other examples, the data determined by the on-board processing system may comprise an indication or measure of a condition, state or one or more properties of the entity, such as a mechanical property or condition.

The on-board processing system may be configured to process the electrical signal or a digitized version of the electrical signal or one or more properties derived from the electrical signal, e.g. by performing one or more of: quantitative analysis, spectral analysis, statistical analysis, application of machine learning or artificial intelligence techniques to determine the data. The artificial intelligence techniques may comprise applying a neural network, such as a regressive neural network, or other learning algorithm. The neural network or other learning algorithm may be trained using training data. The training data may be derived from historical data, data generated by a model and/or data that has been classified by one of the other processing operations, e.g. quantitative analysis, spectral analysis, statistical analysis or by human classification. The neural network or other learning algorithm may map one or more inputs to one or more outputs. The inputs may comprise a digitized version of the electrical signal(s) output by the at least one ultrasonic transducer and/or data derived from the ultrasonic signal, such as amplitude, time of flight, time since emission, attenuation, frequency, frequency shift, Doppler shift, and/or the like, which may be data for one or more or a continuum of times. The outputs may comprise the data that represents a measure or value of the state, property, parameter or condition of the entity.

The on-board processing system may comprise a digitizer or otherwise be configured to digitize the electrical signal from the at least one ultrasonic transducer or values thereof. The processing of the electrical signal(s) generated by the at least one ultrasonic transducers by the on-board processing system may comprise digital processing of the digitized electrical signal or data derived therefrom.

The on-board processing system may be configured to digitally enhance the digitized electrical signal from the at least one ultrasonic transducer or values thereof. The on-board processing system may be configured to filter the digitized electrical signal from the at least one ultrasonic transducer or values thereof, e.g. using matched filtering. The matched filtering may comprise match filtering using a wideband linear or arbitrarily swept chirp signal, which may be applied in a determined or predetermined frequency range, which may be comprised in a frequency range from 0.5 MHz to 1 GHz, e.g. from 1 MHz to 100 MHz.

The on-board processing system may comprise at least one digital data processing module, such as at least one processor (which may include one or more different types of processor such as one or more of a central processing unit (CPU), Graphics Processing Unit (GPU), maths co-processor, a tensor processing unit, neural processing unit or other type of artificial intelligence (AI) accelerator, a physics processing unit, a field programmable gate array (FPGA), application specific integrated circuit (ASIC), a digital signal processor (DSP), and/or the like. The digital data processing module may be configured to receive the digitized electrical signal from the at least one ultrasonic transducer or values thereof and may be configured to process the digitized electrical signal from the at least one ultrasonic transducer or values thereof to determine the data therefrom. The digital data processing module may be configured to determine the data from the digitized electronic signal after digitization of the signal but before transmission of the data to the external processing system using the communications system of the ultrasonic device.

The communication system may preferably comprise a wireless communications system such as a Wi-Fi™, Bluetooth™ or Bluetooth low energy (BLE), ZigBee™, long range wide area network (LoRaWAn), near field communications (NFC), infra-red (IR), optical wireless communications (OWC) or Li-Fi, and/or cellular telephone communications system such as a GSM, 2G, 3G, 4G, 5G, LTE communications system or any successors or further generations thereof, and/or the like. However, in certain applications, a wired communications system may be used. The communication system may be configured to communicate over the internet, which may comprise using a secure communications method such as secure sockets layer (SSL), transport layer security (TLS) or the like.

The ultrasonic device, e.g. the on-board processing system, may be configured to encrypt the data for transmission via the communication system, e.g. using digital cryptographic techniques. The ultrasonic device may comprise or be associated with an identifier, which may be a digital signature. Each external processing system may also be associated with an identifier, such as a digital signature. The data from the ultrasonic device may be transmitted with the identifier for the ultrasonic device and/or the identifier for the external processing system that the data is for. The ultrasonic device may be configured to transmit the data using key encryption, such as public-private key encryption. The ultrasonic device and/or the external processing system and/or the specific entity being monitored may each be associated with their own public and private encryption keys. The transmissions from the ultrasonic device to the external processing system may be encrypted using the public key of the external processing system, which may have been pre-programmed on, or pre-transmitted to, the ultrasonic device. The data generated by the on-board processing system and/or the digitized version of the electrical signals produced by the ultrasonic transducers may be encrypted before storage and/or transmission, e.g. using private encryption keys associated with and/or specific to the ultrasonic device and/or the entity. This may provide control of access to the data to users in possession of the private keys for the ultrasonic device and/or the entity being monitored.

The on-board processing system may have access to measurement metadata, which may be stored in the on-board data store. The on-board processing system may be configured to combine the data with the measurement metadata, e.g. as part of the encryption of the data. The external processing system may also have access to network metadata, and the external processing system may be configured to combine the data with the network metadata, e.g. as part of the encryption of the data.

The integrity of the ultrasonic data may be protected utilising a distributed ledger, such as blockchain, replicated journal technology, hyperledger, directed acyclic graph (DAG) and/or the like. The on-board processing system and/or the external processing system may be configured to store and/or transmit the data generated by the on-board processing system and/or the digitized version of the electrical signals produced by the ultrasonic transducers as the distributed ledger, e.g. as the Blockchain, replicated journal technology, hyperledger, directed acyclic graph (DAG) and/or the like, e.g. in order to protect the integrity of the ultrasonic data. The on-board processing system and/or the external processing system may be configured to protect the ultrasonic data using the distributed ledger before communicating the ultrasonic data, e.g. with the external processing system.

The on-board processing system and/or the external processing system may be configured to group data generated by the on-board processing system and/or the digitized version of the electrical signals produced by the ultrasonic transducers into blocks for transmission or storage. The blocks may comprise a number or predetermined amount of chronologically sequential data generated by the on-board processing system and/or a portion of the digitized version of the electrical signals produced by the ultrasonic transducers.

The on-board processing system and/or the external processing system may be configured to verify any data before including it in a block. The verification may be a verification with one or more external computers, e.g. from a network of computers, which may be a decentralized network of computers.

The on-board processing system and/or the external processing system may be configured to store and/or transmit the data in the blocks, wherein each block comprises one or more items of data, e.g. data associated with one or more different types of ultrasonic measurements for a given time or for a plurality of different times. The data may be time stamped data, e.g. time stamped with the time the data was collected or processed. The on-board processing system and/or the external processing system may be configured to strictly process and/or transmit the data in blocks in an order, e.g. in a chronological order, such as in an order of when data was collected by the ultrasonic device or processed by the on-board processing system. The on-board processing system and/or the external processing system may be configured to generate a unique code or identifier for each block.

The on-board processing system and/or the external processing system may be configured to encrypt and/or encode the data, e.g. the blocks of data, and/or generate a hash of at least the data in the block before transmitting or storing the data or block.

The on-board processing system and/or the external processing system may be configured to hash, encrypt and/or encode the data, e.g. each block of data, in a manner that requires knowledge or decoding of at least one preceding block or datum, e.g. at least the immediately preceding block or datum, optionally a plurality of preceding blocks or data, and optionally all preceding blocks or data.

The hash may be generated using a secure hashing algorithm such as, but not limited to, SHA-256. The secure hashing algorithm may be an algorithm that is deterministic, irreversible and/or collision resistant. The hash may be a fixed length hash, regardless of the length of the input data. The hash for a given block may be a hash of data comprising the hash for the previous block and/or at least some or all of the data from a previous block and/or data from the present block.

In this way, the data provided by the ultrasonic device may be made more tamper resistant, which may improve the dependability of the data, particularly for applications that require highly verifiable or tamper proof data.

The on-board processing system and/or the external processing system may be configured to encode or encrypt the data or blocks of data using blockchain, distributed acyclic graph, distributed ledger technology, hyperledger, or other cryptocurrency or distributed ledger techniques.

The communication system may be configured to communicate the data with the external processing system directly or indirectly, e.g. via one or more relay or intermediate communications devices such as routers, mobile base stations, switching stations and/or the like.

In some examples, the external processing system may be a remote data processing system. The external processing system may be in communication with the ultrasonic device over a network, such as a wide area network or the internet. The external processing system may be located in a different location and/or a different room or building and/or in the order of tens or hundreds of metres away from the ultrasonic device, or several miles away, and/or the like, from the ultrasonic device. In some examples, the external processing system may be local to the ultrasonic device, e.g. at the same location, within the same building, or in the order of cm's or metres, or in single cable range.

The external processing system may be or comprise a server or group of servers, a cloud computing resource, a dedicated or bespoke computing resource, a workstation, a personal computer, a computer system that runs Unix or Linux, or other high capacity computing system.

The external processing system may be configured to further process the data received from the ultrasonic device, e.g. to derive further data from the data received from the ultrasonic device. The external processing system may configured to store the data generated by the on-board processing system and/or the digitized version of the electrical signals produced by the ultrasonic transducers, e.g. in centralized data storage. The centralized storage may store the data generated by the on-board processing system and/or the digitized version of the electrical signals produced by the ultrasonic transducers in the distributed ledger, e.g. in the blockchain or DAG. The centralized storage may store the encrypted version of the data generated by the on-board processing system and/or the digitized version of the electrical signals produced by the ultrasonic transducers.

The external processing system may configured to distribute the data or further data, e.g. to one or a plurality of computing resources. The external processing system may configured to distribute the data or further data in the distributed ledger and/or in encrypted form. The computing resources may be or comprise at least one user device, smartphone, personal computer, laptop computer, tablet computing device, control or monitoring system, server computer, computer workstation, cloud computing resource, and/or the like. The computing resources may be configured to access or receive the data and/or further data from the external computing resource. The data and/or further data may be pushed to the computing resources by the external computing system or pulled from the external computing system by the computing resources. The further data may comprise an alarm or alert indicator, an alarm or alert state, an alarm or alert value or magnitude, an alarm or alert type, and/or further information supporting the alarm or alert. The alarm or alert may be representative of a condition, state, or property of the entity being monitored by the ultrasonic device. The alarm may be provided "on the fly" and/or in real time or near real time, at least within the limits of the processing and data transmission.

The computing resources may comprise one or more of: at least one display, an audio system, a haptic system, at least one visual indicator, and/or the like. The computing resources may be configured to provide the data and/or further data or a representation or indicator thereof, or an alarm, alert or condition update based on the data or further data, e.g. using the display, the audio system, the haptic system, the visual indicator, and/or the like. The representation may comprise a graph, chart, table or other graphical indicator, but is not limited to those.

The computing resources and/or the external computing system may provide the alarm or alert and/or data and/or further data at a location that is remote or different to the location of the ultrasonic device, e.g. at a location of a monitoring service, a doctor or other medical professional or system, a care giver, a support worker, a nominated person, an operator or controller, and/or the like.

The ultrasonic device may be configured to remain attached to the entity, e.g. to collect ultrasonic measurements of the entity over time, e.g. to determine changes and/or evolution of the data and/or one or more of the properties or parameters of the entity with time.

The ultrasonic device may comprise a power source for powering the at least one ultrasonic transducer, the on-board processing system, the communications system, and/or the data storage. The power source may comprise power storage such as a battery, a fuel cell, a flow cell or other electro-chemical power storage device, a capacitor, super-capacitor or other electrostatic storage device, and/or or the like. The power source may comprise an inductive or other wireless charging or power receiving system. The power source may comprise a mechanical power source, such as a kinetic power source.

The ultrasonic device may comprise an array of ultrasonic transducers and the at least one ultrasonic transducer may be comprised in the array.

The ultrasonic transducer(s) or the array of ultrasonic transducers may comprise a layer of piezoelectric material on a substrate. The ultrasonic transducers may be flexible ultrasonic transducers. The substrate may comprise a conductive substrate such as a metallic foil.

The piezoelectric material may be or comprise a primary piezoelectric material such as a metal oxide or metal nitride, such as zinc oxide or aluminium nitride, or a doped or alloyed metal oxide or metal nitride. The piezoelectric material may comprise a dopant or further material (such as an alloying material or a co-deposited material), which may be or comprise a transition metal or compound thereof. The dopant or further material may be vanadium, for example. The dopant or further material may be present in the piezoelectric material at a level up to 10% with respect to weight, e.g. from 0.01 to 10% w/w. The primary piezoelectric material, e.g. the metal oxide or metal nitride, may be present in the layer of piezoelectric material in levels from 90% w/w up to 99.99% w/w. In other examples, the ultrasonic transducers may be other types of transducers, such as ceramic, PZT, polymeric or other transducers, and may be single crystal or polycrystalline, and that the transducers may not necessarily be flexible or thin film.

The layer of piezoelectric material may be, comprise or be comprised in a film of piezoelectric material. The layer of piezoelectric material may be configured and/or operable to produce ultrasound, i.e. the layer of piezoelectric material may be or comprise an ultrasound production layer. The ultrasound may be sound waves having a frequency greater than 20 kHz, e.g. from 100 kHz up to 2 or 5 Gigahertz. The piezoelectric material may be or comprise an inorganic material. The piezoelectric material may be a crystalline, e.g. polycrystalline or columnar, piezoelectric material. The layer of piezoelectric material may be a layer of non-polymeric piezoelectric material. However, depending on the application, the piezoelectric material may be or comprise a thin film, ceramic, MEMS, polymeric or ceramic piezoelectric material. The piezoelectric material may be or comprise a continuous layer of material having piezoelectric properties, e.g. the piezoelectric material may not comprise discrete domains of piezoelectric material having piezoelectric properties within a matrix of non-piezoelectric material. The layer of piezoelectric material may have a thickness in the range of 2 to 20 μm. The layer of piezoelectric material may be thinner than the substrate, e.g. at least 2, 5, 6 or 10 times thinner than the substrate. However, the disclosure is not limited to thin film flexible transducers having the composition above and, in other examples, the ultrasonic transducers may be or comprise other types of transducers, such as ceramic, PZT, polymeric or other transducers.

The ultrasonic transducer(s) or the array of ultrasonic transducers may comprise at least one electrode on the layer of piezoelectric material, which may be comprised in an electrode array on the layer of piezoelectric material. The electrodes may be working electrodes. Each electrode in the array may represent a different ultrasonic transducer, e.g. in the array of ultrasonic transducers. The ultrasonic device may comprise at least one electrical conduction track and/or at least one electrical connector, e.g. on the surface of the piezoelectric material or on an electrically resistive layer disposed thereon. Respective electrical conduction tracks may electrically connect a respective electrode to a respective electrical connector. However, other arrangements for providing electrodes and/or electrically connecting the electrodes and/or electrically coupling the layer of piezoelectric material may be used.

The substrate may be electrically conductive, i.e. it may be an electrical conductor. The substrate may be planar. The substrate may be a film or sheet. The substrate may be metallic, e.g. a metal film. The substrate may be or comprise a metal or metallic foil such as aluminium foil. The substrate may be or comprise a thin foil. The substrate may have a thickness in the range of 20 to 200 μm. The substrate may be thicker than the layer of piezoelectric material, e.g. by at least a factor of 6 or by a factor of 10 or more.

The substrate may be, comprise, or be comprised in an electrical ground electrode. The substrate may be, comprise, or be comprised in a counter electrode to the working electrode(s). The counter or ground electrode may form an electrode pair with the at least one working electrode (e.g. the working electrodes of the electrode array), which may be provided on an opposing side of the piezoelectric material to the counter or ground electrode. A surface of the substrate that is opposite to a surface of the substrate upon which the layer of piezoelectric material is disposed may be a radiating surface from which ultrasonic waves are radiated in use.

The ultrasonic transducer(s) or array of ultrasonic transducers may comprise a secondary layer. The secondary layer may comprise an encapsulating material. The secondary layer may be or comprise a dielectric material. The secondary layer may be or comprise a polymeric material, such as a dielectric polymer. The secondary layer may be thinner than the substrate. The secondary layer may be less than 50 μm thick, e.g. between 1 and 50 μm thick. The secondary layer may comprise or be formed from an epoxy, a polyimide, a poly para-xylene, or the like. The secondary layer may be provided directly on, over or overlying at least part of a surface of the layer of piezoelectric material. The secondary layer may be provided directly on, over or overlying an opposite side of the layer of piezoelectric material to the substrate. The secondary layer may be provided directly on, around and/or between at least part or all of the electrical conduction tracks and/or the at least one electrode (e.g. the electrodes of the array of electrodes). The secondary layer may be electrically insulating. The secondary layer may leave at least part or all of the connectors exposed. The secondary layer may be provided only on the piezoelectric material and/or the electrically conducting material that forms the electrical conduction tracks and/or the at least one electrode. The secondary layer may not be directly provided on the substrate or at least not directly on the side of the substrate that is opposite the side of the substrate upon which the piezoelectric material is provided.

The ultrasonic transducer(s) or array of ultrasonic transducers may have a bandwith that is greater than 100%, with a centre of frequency of the bandwidth being greater than 10 MHz.

The ultrasonic transducer may be an ultrasonic transducer for testing, such as non-destructive testing. The ultrasonic transducer may be an ultrasonic transducer for imaging, such as ultrasound imaging.

According to a second example of the present disclosure is a system comprising one or more of the ultrasonic devices of the first example and an external processing system, wherein the ultrasonic device(s) are configured to communicate ultrasonic data with the external processing system, e.g. using the communications system of the respective ultrasonic device. The system may be configured to protect the integrity of the ultrasonic data utilising a distributed ledger, such as blockchain, replicated journal technology, hyperledger, directed acyclic graph (DAG) and/or the like.

At least one or each of the ultrasonic devices (e.g. the respective on-board processing system of the respective ultrasonic device) may be configured to process processing the electrical signal collected by the at least one ultrasonic transducer of the respective ultrasonic device to determine data therefrom. At least one or each of the ultrasonic devices (e.g. the respective communications system of the respective ultrasonic device) may be configured to communicate the data (e.g. digital data derived from an analogue ultrasound signal) determined by the on-board processing system to the external processing system.

The on-board processing system and/or the external processing system may be configured to store and/or transmit the data generated by the on-board processing system and/or the digitized version of the electrical signals produced by the ultrasonic transducers as the distributed ledger, e.g. as the Blockchain, replicated journal technology, hyperledger, directed acyclic graph (DAG) and/or the like, e.g. in order to protect the integrity of the ultrasonic data. The on-board processing system and/or the external processing system of the at least one or each ultrasonic devices may be configured to protect the integrity of the ultrasonic data utilising a distributed ledger before communicating the ultrasonic data, e.g. with the external processing system and/or the internal processing system of the at least one or each of the ultrasonic devices.

The on-board processing system and/or the external processing system may be configured to group data generated by the on-board processing system and/or the digitized version of the electrical signals produced by the ultrasonic transducers into blocks for transmission or storage. The blocks may comprise a number or predetermined amount of chronologically sequential data generated by the on-board processing system and/or a portion of the digitized version of the electrical signals produced by the ultrasonic transducers.

The on-board processing system and/or the external processing system may be configured to verify any data before including it in a block. The verification may be a verification with one or more external computers, e.g. from a network of computers, which may be a decentralized network of computers.

The on-board processing system and/or the external processing system may be configured to store and/or transmit the data in the blocks, wherein each block comprises one or more items of data, e.g. data associated with one or more different types of ultrasonic measurements for a given time or for a plurality of different times. The data may be time stamped data, e.g. time stamped with the time the data was collected or processed. The on-board processing system and/or the external processing system may be configured to strictly process and/or transmit the data in blocks in an order, e.g. in a chronological order, such as in an order of when data was collected by the ultrasonic device or processed by the on-board processing system. The on-board processing system and/or the external processing system may be configured to generate a unique code or identifier for each block.

The on-board processing system and/or the external processing system may be configured to encrypt and/or encode the data, e.g. the blocks of data, and/or generate a hash of at least the data in the block before transmitting or storing the data or block.

The on-board processing system and/or the external processing system may be configured to hash, encrypt and/or encode the data, e.g. each block of data, in a manner that requires knowledge or decoding of at least one preceding block or datum, e.g. at least the immediately preceding block or datum, optionally a plurality of preceding blocks or data, and optionally all preceding blocks or data.

The hash may be generated using a secure hashing algorithm such as, but not limited to, SHA-256. The secure hashing algorithm may be an algorithm that is deterministic, irreversible and/or collision resistant. The hash may be a fixed length hash, regardless of the length of the input data. The hash for a given block may be a hash of data comprising the hash for the previous block and/or at least some or all of the data from a previous block and/or data from the present block.

In this way, the data provided by the ultrasonic device may be made more tamper resistant, which may improve the dependability of the data, particularly for applications that require highly verifiable or tamper proof data.

The on-board processing system and/or the external processing system may be configured to encode or encrypt the data or blocks of data using blockchain, distributed acyclic graph or other cryptocurrency or distributed ledger techniques.

In some examples, the external processing system may be a remote data processing system. The external processing system may be in communication with the ultrasonic device over a network, such as a wide area network or the internet. The external processing system may be located in a different location and/or a different room or building and/or in the order of tens or hundreds of metres away from the ultrasonic device, or several miles away, and/or the like, from the ultrasonic device. In some examples, the external processing system may be local to the ultrasonic device, e.g. at the same location, within the same building, or in the order of cm's or metres, or in single cable range.

The external processing system may be or comprise a server or group of servers, a cloud computing resource, a dedicated or bespoke computing resource, a workstation, a personal computer, a computer system that runs Unix or Linux, or other high capacity computing system.

The external processing system may be configured to further process the data received from the ultrasonic device, e.g. to derive further data from the data received from the ultrasonic device. The external processing system may configured to store the data generated by the on-board processing system and/or the digitized version of the electrical signals produced by the ultrasonic transducers, e.g. in centralized data storage. The centralized storage may store the data generated by the on-board processing system and/or the digitized version of the electrical signals produced by the ultrasonic transducers in the distributed ledger, e.g. in the blockchain or DAG. The centralized storage may store the encrypted version of the data generated by the on-board processing system and/or the digitized version of the electrical signals produced by the ultrasonic transducers.

The external processing system may configured to distribute the data or further data, e.g. to one or a plurality of computing resources. The external processing system may configured to distribute the data or further data in the distributed ledger and/or in encrypted form. The computing resources may be or comprise at least one user device, smartphone, personal computer, laptop computer, tablet computing device, control or monitoring system, server computer, computer workstation, cloud computing resource, and/or the like. The computing resources may be configured to access or receive the data and/or further data from the external computing resource. The data and/or further data may be pushed to the computing resources by the external computing system or pulled from the external computing system by the computing resources. The further data may comprise an alarm or alert indicator, an alarm or alert state, an alarm or alert value or magnitude, an alarm or alert type, and/or further information supporting the alarm or alert. The alarm or alert may be representative of a condition, state, or property of the entity being monitored by the ultrasonic device. The alarm may be provided "on the fly" and/or in real time or near real time, at least within the limits of the processing and data transmission.

The computing resources may comprise one or more of: at least one display, an audio system, a haptic system, at least one visual indicator, and/or the like. The computing resources may be configured to provide the data and/or further data or a representation or indicator thereof, or an alarm, alert or condition update based on the data or further data, e.g. using the display, the audio system, the haptic system, the visual indicator, and/or the like. The representation may comprise a graph, chart, table or other graphical indicator, but is not limited to those.

The computing resources and/or the external computing system may provide the alarm or alert and/or data and/or further data at a location that is remote or different to the location of the ultrasonic device, e.g. at a location of a monitoring service, a doctor or other medical professional or system, a care giver, a support worker, a nominated person, an operator or controller, and/or the like.

According to a third example of the present disclosure is a method of determining and/or monitoring properties of an entity using at least one of the ultrasonic devices of the first example or the system of the second example. The method may comprise emitting an ultrasonic signal from the ultrasonic device (e.g. from one or more or each of the at least one ultrasonic transducer of the ultrasonic device) into or onto the entity. The method may comprise receiving an ultrasonic signal using the ultrasonic device (e.g. at one or more or each of the at least one ultrasonic transducer of the ultrasonic device), wherein the received signal may comprise or be derived from the signal emitted into or onto the entity, e.g. a reflection of the signal emitted into or onto the entity. The received signal may comprise a reflection of the signal emitted into or onto the entity by one or more interfaces on or in the entity. The method may comprise deriving or determining ultrasonic data from the received signal. The method may comprise protecting the integrity of the ultrasonic data utilising a distributed ledger, such as blockchain, replicated journal technology, hyperledger, directed acyclic graph (DAG) and/or the like. The method may comprise protecting the integrity of the ultrasonic data utilising a distributed ledger before communicating the ultrasonic data, e.g. with the external processing system and/or the internal processing system of the at least one or each of the ultrasonic devices.

According to a fourth example of the present disclosure is a computer program product that, when implemented on a controller or the on-board processing system of the ultrasonic device of the first aspect, causes the controller or on-board processing system to control the ultrasonic device to perform the method of the third example.

The individual features and/or combinations of features defined above in accordance with any aspect of the present invention or below in relation to any specific embodiment of the invention may be utilised, either separately and individually, alone or in combination with any other defined feature, in any other aspect or embodiment of the invention.

Furthermore, the present invention is intended to cover apparatus configured to perform any feature described herein in relation to a method and/or a method of using, producing, repairing or manufacturing any apparatus feature described herein. For any of the apparatus features described above as performing a function, the present invention also covers a method comprising performing that function.

BRIEF DESCRIPTION OF THE DRAWINGS

These and other aspects of the present disclosure will now be described, by way of example only, with reference to the accompanying Figures, in which.

DETAILED DESCRIPTION OF THE DRAWINGS

Ultrasound is a well-known imaging technique in medicine. However, current imaging systems are expensive and complex for mass produced wearable devices and as such are generally confined to hospital and other facilities. However, the advent of low cost, mass producible and flexible transducers such as those described in WO 2019/166805, WO 2019/166815 and PCT/GB2020/050468 in the name of the present applicant, the contents of which are incorporated by reference as if set out in full herein, has opened up a variety of new possibilities. These include opportunities to use ultrasound measurements in monitoring, where devices can be left in situ on an entity to be monitored over an extended period of time, such as over several hours, days, week or even years. In this way, the time evolution of one or more properties of the entity can be determined and monitored using ultrasound techniques. The new devices also give rise to the possibility of use in wearable technology, which can allow the opportunity to monitor the condition of living entities. This could, for example, allow such wearable ultrasound sensors to monitor the condition of humans and animals, which may involve identification, monitoring and/or alerting of the conditions or other physiological or medical parameters.

Figure 1:
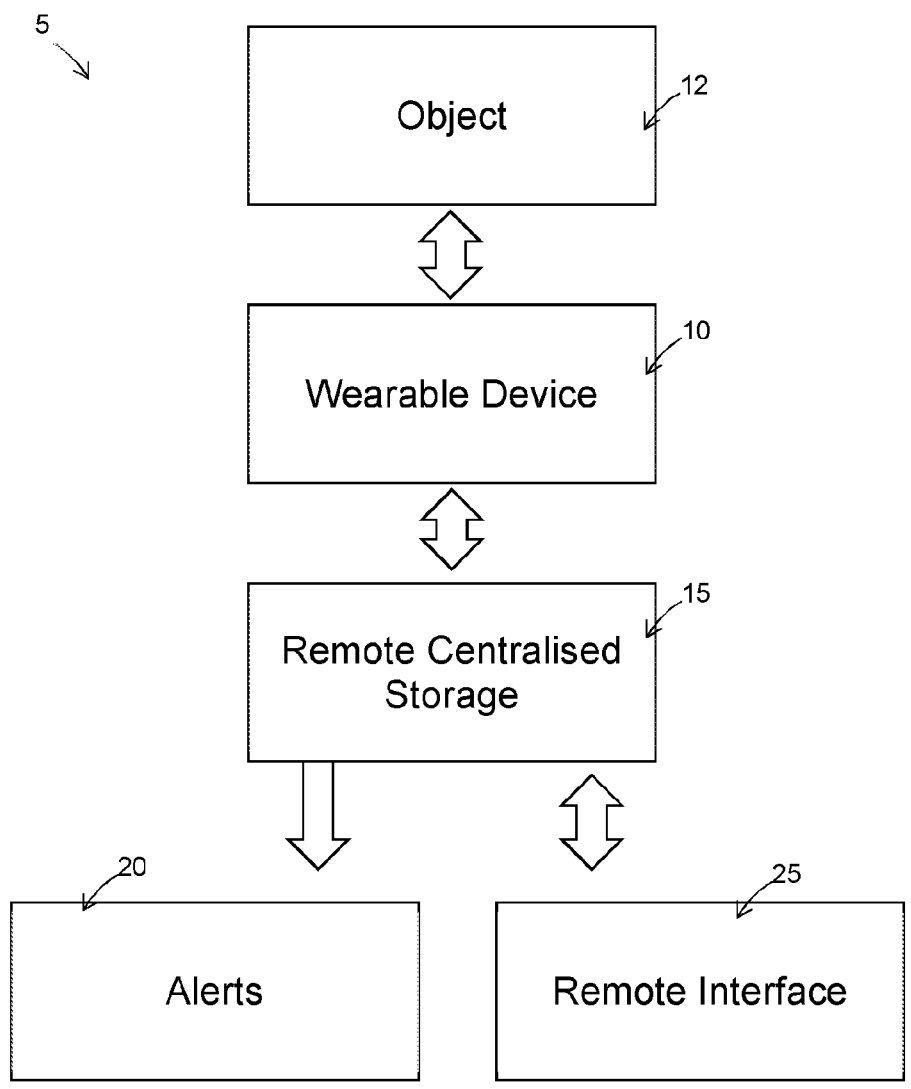
FIG. 1 is a high-level overview of an ultrasound monitoring system.
Figure 2:
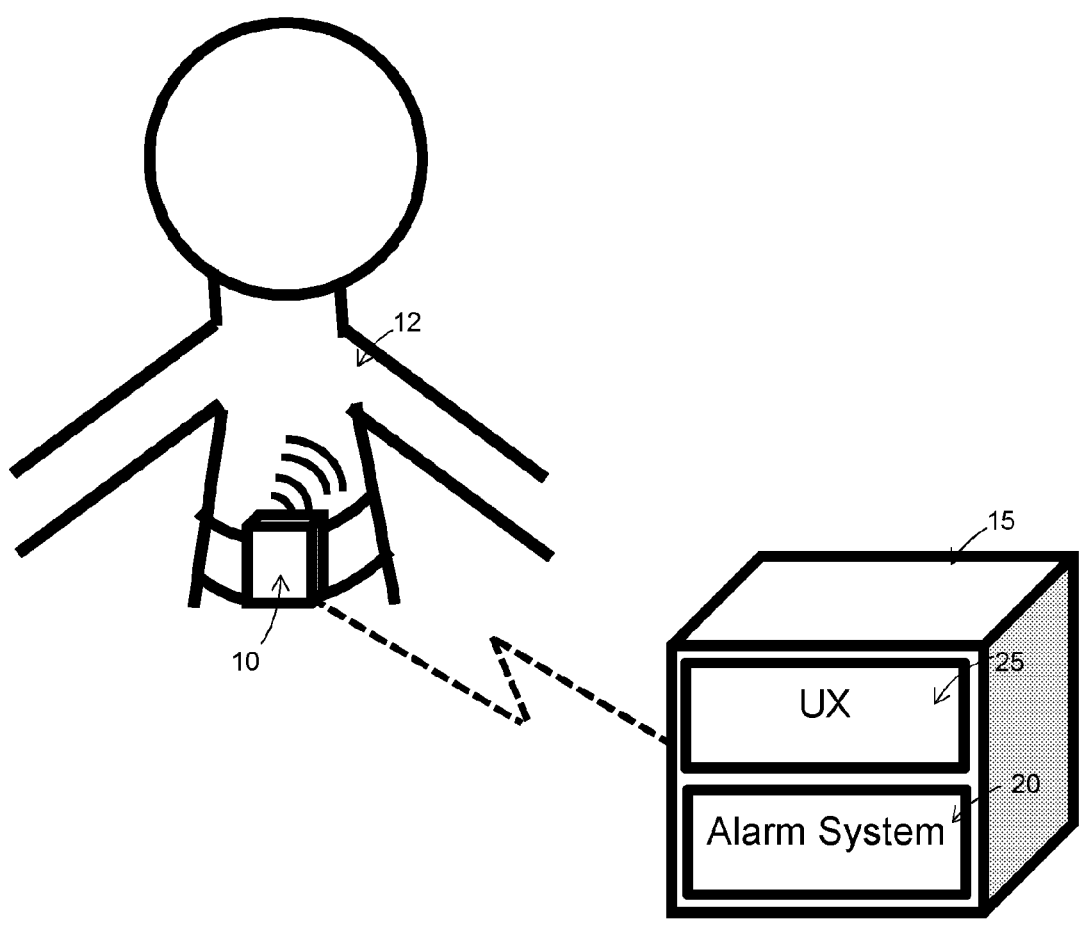
FIG. 2 shows an application of the ultrasound monitoring system of FIG. 1.

An ultrasound system 5 that is capable of providing monitoring functionality is shown in FIGS. 1 and 2. The ultrasound system 5 comprises at least one ultrasonic device 10 for monitoring a respective entity or object 12. In this example, the ultrasonic device 10 is a wearable ultrasonic device 10 that can be worn by humans or animals, i.e. the entity or "object" 12 is a living creature. However, the applications are not limited to this and the ultrasound device 10 could equally be mounted to and monitor a pipe, support, beam, a part of a building or other architectural structure, a piece of plant or machinery, a wind turbine or tower, a naval or sea based structure, or a part of a vehicle, amongst a number of other suitable possibilities.

The ultrasonic device 10 is configured to provide processing functionality, i.e. edge processing, and can implement digitization of the analogue ultrasound signal and processing of the digital signal such as signal processing, quantitative analysis, statistical analysis, spectral analysis, artificial intelligence, and/or the like. Edge processing allows processed digital information, rather than raw data, to be transmitted to an external processing system 15 for remote monitoring and diagnosis of diseases and conditions such as pneumonia, chest infections, dehydration, muscle damage, skin damage, digestive health issues, cardiac dysfunction and other health complaints. The external processing system 15 comprises remote data storage of the digital information collected by the ultrasonic device 10 and potentially a number of other ultrasonic devices 10. The information can be analysed by the external processing system 15 to provide an alert 20 that a certain condition of the entity or object 12 has arisen (and optionally alert that assistance is required). The external processing system is also configured to provide a remote user interface 25 for interrogating the information returned from the one or more ultrasonic devices 10 and any other ultrasonic devices 10 regarding the respective entity or object 12 on which they are mounted or associated.

Figure 3:
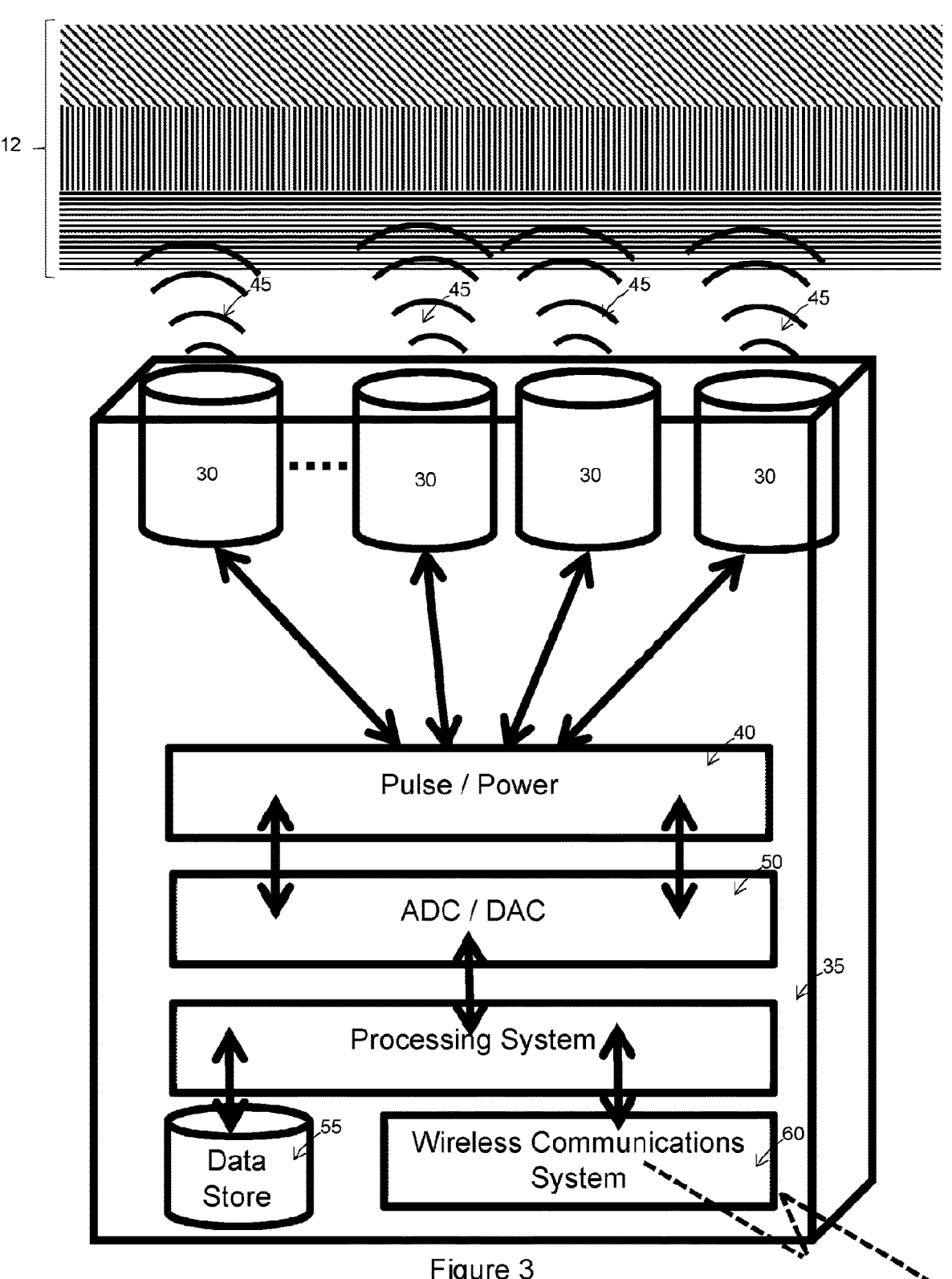
FIG. 3 is a schematic of an ultrasonic device for use in the system of FIGS. 1 and 2.

A more detailed schematic of the ultrasonic device 10 is shown in FIG. 3. The ultrasonic device 10 comprises a plurality of ultrasound transducers 30 ultimately connected to an on-board processing system 35. The on-board processing system 35 could comprise one or more processors, such as a central processing unit, graphics processing unit (GPU), maths co-processor, tensor processing unit, neural processing unit or other type of artificial intelligence (AI) accelerator, a physics processing unit, a field programmable gate array (FPGA), application specific integrated circuit (ASIC), a digital signal processor (DSP), and/or the like. The on-board processing system 35 is configured to provide edge processing functions such as signal processing, quantitative analysis, statistical analysis, spectral analysis, artificial intelligence, and/or the like.

The array of ultrasonic transducers 30 can beneficially be flexible thin film transducers based on a non-polymeric, polycrystalline piezoelectric material, such as ZnO or AlN, deposited onto a conductive, flexible substrate, such as a metallic foil. Examples of suitable ultrasonic transducers 30 are described in WO 2019/166805, WO 2019/166815 and PCT/GB2020/050468 in the name of the present applicant, the contents of which are incorporated by reference as if set out in full herein.

The ultrasonic transducers 30 are operated by a pulse/power module 40 that can supply pulsed electrical waveform signals to cause the ultrasonic transducers 30 to vibrate at ultrasonic frequencies to produce corresponding ultrasound waves 45 that are transmitted into the entity or object 12 (see also FIGS. 1 and 2). Reflections of the ultrasonic waves 45 from boundaries between regions of different acoustic impedance within the entity or object 12 are in turn received by the ultrasonic transducers 30. This causes the piezoelectric material to produce a corresponding analogue electrical signal that is indicative of the frequency and amplitude of the received ultrasonic waves 45.

The ultrasonic device 10 comprises a digitizer 50 in the form of an analogue to digital converter that is operable to convert the analogue electrical signal produced by the ultrasonic transducers 30 into a digital signal that can be processed by the on-board processing system 35.

The on-board processing system 35 receives the digitized versions of the electrical signal originally generated by the ultrasonic transducers 30 from the digitizer 50 and processes the digitized electrical signal to determine properties of the entity or object 12. It will be appreciated that the electrical signal produced by the ultrasonic transducers 30 is representative of properties of the received ultrasound, such as amplitude and frequency over time. The on-board processing system is configured to derive parameters from the signal, such as time of flight/time between transmission of the emitted ultrasonic wave and reception of each of the reflections from the boundaries of the entity or object 12, Doppler shift, and/or the like. The on-board processing system is configured to determine properties of the entity or object 12 from the received ultrasound signals. Non-limiting examples of such properties could include such as the location of the boundaries, the density of regions of the entity or object, lung capacity or fill of the entity, blood flow rate, heart rate, breathing rates, muscle density and/or the like, form among a number of possible properties.

The values of the properties of the entity or object determined by the on-board processing system 35 can be temporarily or persistently stored in on-board data storage 55 that is comprised in the ultrasonic device 10. Additionally or alternatively, the values of the properties of the entity or object determined by the on-board processing system 35 can be transmitted, preferably wirelessly transmitted, directly or indirectly by a communications system 60 comprised in the ultrasonic device 10 to the external processing system 15 for further storage, processing, distribution, display on the remote user interface 25 and/or for raising an alarm 20 if the values of the properties of the entity or object are indicative of an alarm-worthy condition. In this way, the ultrasonic device 10 can be mounted on the entity or object 12 to perform ultrasound measurements over time on the entity or object 12, determine the corresponding values of one or more properties of the entity or object 12 on board the ultrasonic device 10 and then transmit the values of the one or more properties of the entity to the external processing system 15. The external processing system 15 can then provide remote access, alarms 20, centralized storage of the values, data distribution, and/or the like.

Figure 4:
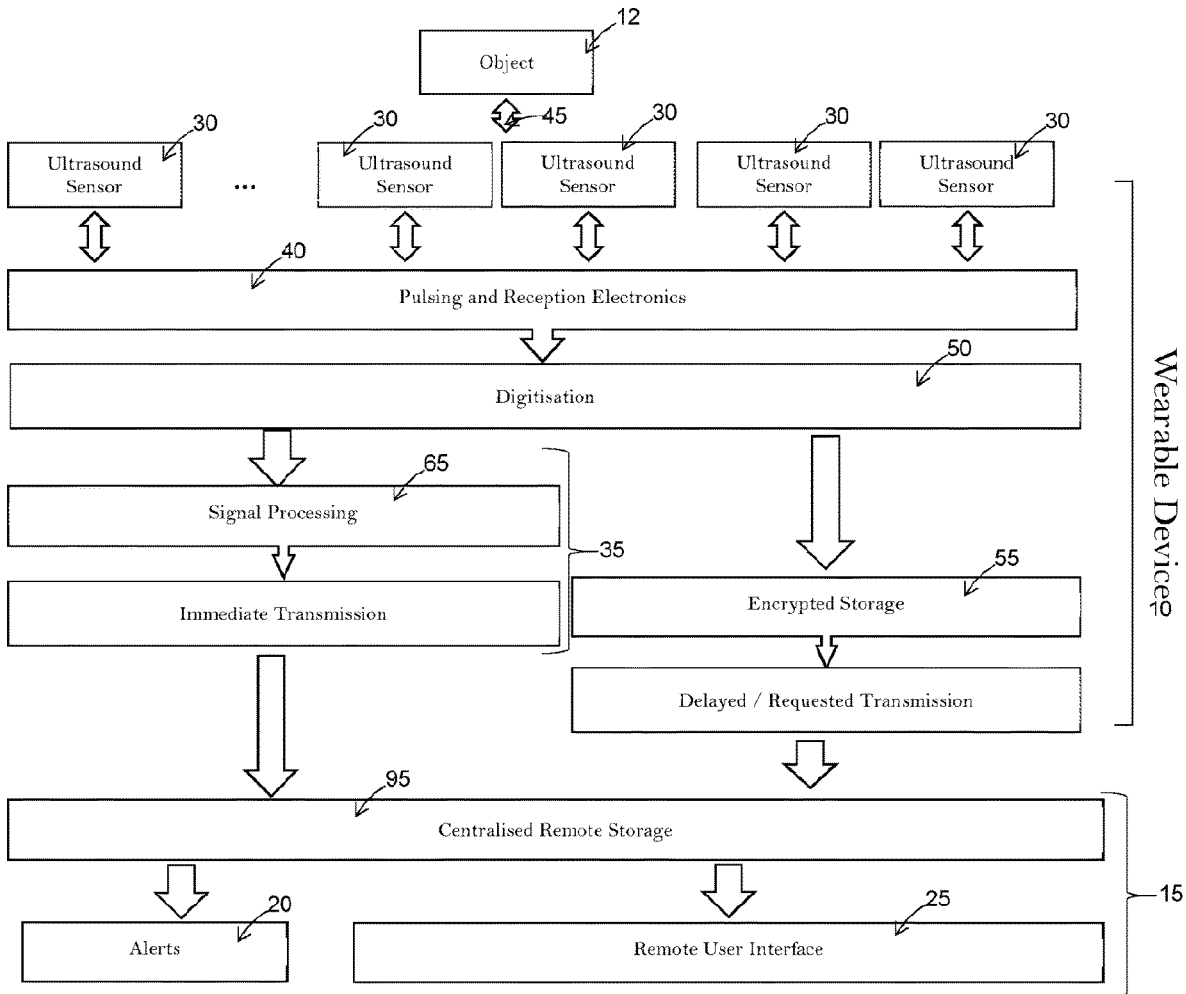
FIG. 4 is a detailed schematic showing the flow of data in the system of FIG. 1.

A more detailed view of the system of FIG. 1 is shown in FIG. 4. From this, it can be seen that, in use, the wearable ultrasonic device 10 is mounted onto the entity or object 12. In particular, the ultrasonic device 10 can comprise straps, bands, clips, or other fixings for fixing the ultrasonic device 10 to the entity or object 12 or the ultrasonic device can be provided in a wearable item such as a helmet or garment. At least some of the array of ultrasonic transducers 30 of the ultrasonic device 10 are adapted to engage an outer surface of the entity or object 12 in order to emit ultrasound pulses into the entity or object 12 under operation from the pulsing and power module 40 and receive reflections of the ultrasound pulses back in order to generate the corresponding analogue electrical signal. The corresponding electrical signal is digitized by the digitizer 50 and provided to the on-board processing system 35.

The on-board processing system 35 is configured to derive the values of the one or more properties of the entity or object 12 and send it for immediate wireless transmission via the communications system 60 of the ultrasonic device 10 to the external processing system 15 in a secure manner, as will be described later. Optionally, such determinations can be on-the fly and in real time or almost real time and transmitted immediately. This allows for faster alert or alarm 20 raising.

The on-board data storage 55 on the ultrasonic device allows the digitized ultrasound data and/or the values of the properties of the entity or object 12 determined by the on-board processing system 35 to be at least temporarily stored on the ultrasound device, e.g. for batch transmission or interrogation on demand or pulled by the external processing system 15. The data stored on the on-board data storage 55 is encrypted, e.g. using private encryption keys associated with the entity or object 12 and/or the specific ultrasonic device 10 and optionally by combining the data with measurement metadata. Thereafter, the data and/or the values of the properties of the entity or object 12 stored in the on-board storage 55 can be transmitted (e.g. "pushed") to the external processing system 15 in a secure manner, as will be described later, via the communications system 60 of the ultrasonic device 10. Alternatively, the data and/or the values of the properties of the entity or object 12 stored in the on-board storage 55 can be "pulled" from the on-board storage 55 on the ultrasonic device by the external processing system 15 in a secure manner, as will be described later, via the communications system 60 of the ultrasonic device 10.

As previously discussed, the external processing system 15 can receive the data and/or the values of the properties of the entity or object 12 determined by the on-board processing system 35 or each ultrasonic device 10. In this way, the external processing system 15 can add additional benefits to the edge processing performed on the ultrasonic devices 10. For example, the external processing system 15 can act as centralized remote storage for the data and/or the values of the properties of each entity or object 12 monitored by one of the ultrasonic devices 10. In this way, multiple entities 12/ultrasonic devices 10 can be monitored by simply accessing the external processing system 15 via a single remote user interface 25. Furthermore, the external processing system 15 can perform further processing on the data and/or the values of the properties of the entities or objects 12, e.g. to determine data, trends and parameters that depend on multiple entities or objects 12 or depend on the correlation between different entities or objects 12. In addition, the external processing system is configured to raise an alert or alarm in response to the determined values of the properties of the entities or objects 12 meeting an alarm condition. This may allow remote workers, such as carers, family, doctors or other medical professionals, monitoring services and the like to be made aware of determined conditions that may require action. In examples, the alert may comprise a message, an email, a pop-up notification, operation of a light or other visual indicator, an audible indicator, a haptic indicator and/or the like. The external processing system may raise the alert by automatically electronically signalling a user device over a network or internet when the determined data meets the alert or alarm conditions.

Figure 5:
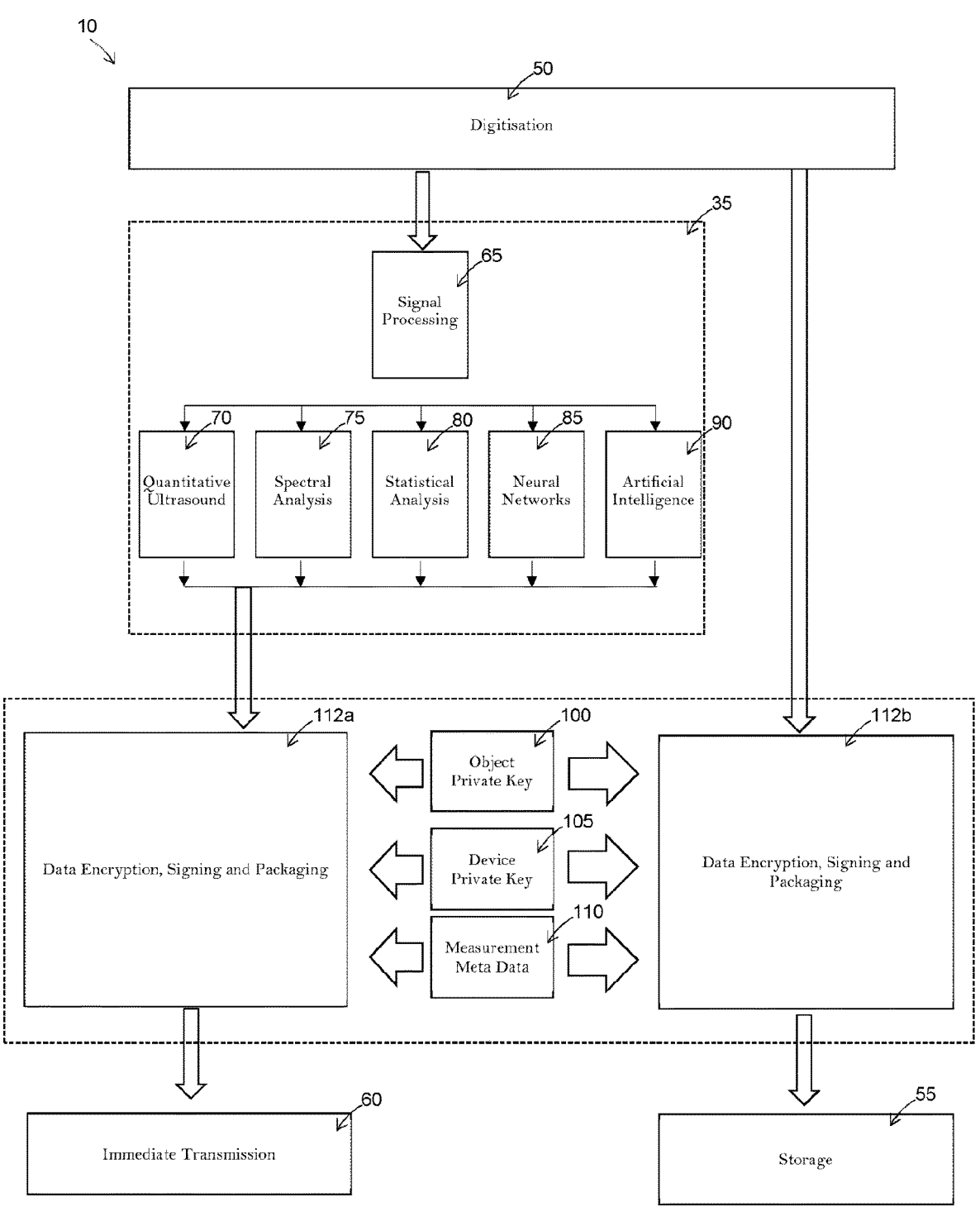
FIG. 5 is a detailed schematic further detailing the flow of data shown in FIG. 4 that is performed on an ultrasonic device.

FIG. 5 is a more detailed representation of those processes shown in FIG. 4 that involve the on-board processing system 35 on the ultrasonic devices 10. FIG. 5 shows the digitizer 50 that digitizes the analogue electrical signal generated by the ultrasonic transducers responsive to the received ultrasound. As can be seen from FIG. 5, the digitized data can be directly encrypted, signed and packaged 112*b* for transmission from the ultrasonic device 10, e.g. to the external processing system 15. Data security is critical in such cases and this will be discussed later.

As can also be seen from FIG. 5, the digitized data is also analysed by the on-board processing system 35 in order to determine values or parameters of the entity or object 12 that are reflected in the received ultrasound.

The digitized data is first processed by signal processor 65. The signal processor 65 can be configured to process the digitized electrical signal from the ultrasonic transducers 30, e.g. to convert it into a useable form by the later processes. This could comprise, for example, digitally enhancing the digitized electrical signal, e.g. by filtering the digitized electrical signal from the at least one ultrasonic transducer, such as by using matched filtering. The matched filtering may comprise match filtering using a wideband linear or arbitrarily swept chirp signal, which may be applied in a determined or predetermined frequency range, which may be comprised in a frequency range from 0.5 MHz to 1 GHz, e.g. from 1 MHz to 100 MHz. However, the digital enhancement processes are not limited to this and other processes known in the art could be used. The signal processing could optionally involves processing the digitized signal in order to extract properties of the signal, e.g. signal amplitude over time, times and locations associated with peaks in amplitude, frequency of the signal, changes in frequency of the signal over time, Doppler shifts, and the like. The output of the signal processor 60, such as the determined properties of the signal, are then subjected to further processing in order to determine the values of the properties of the entity or object 12.

One or more different types of analysis can be used to process the output of the signal processor 65 to determine the values of the properties of the entity or object 12, as would be apparent to one skilled in the art. For example, the values of the properties of the entity or object 12 may be determined qualitatively 70, e.g. using techniques such as Doppler shift analysis or by using time of flight analysis to determine the distance travelled by the ultrasound through the entity or body 12 before being reflected to thereby determine the location of interfaces between regions of different acoustic impedance. In another example, the values of the properties of the entity or object 12 can be determined by applying a spectral analysis 75 to the output of the signal processor to determine the values of the properties of the entity or object 12, for example, by analysing changes in frequency or frequency distribution in the ultrasound during transit through the entity or body 12. In another example, the values of the properties of the entity or object 12 may be determined by applying a statistical analysis 80 to the output of the signal processor to determine the values of the properties of the entity or object 12, e.g. based on probabilistic techniques. In other examples, neural networks or artificial intelligence techniques such as deep learning can be used to determine the values of the properties of the entity or object 12. In these cases, training data can be used to train the neural network to correctly determine the values of the properties of the entity or object 12 (as an output of the neural network) from the digitized and processed ultrasound signals (as an input of the neural network. Examples of training data include data from historical measurements or from models or simulation. Other examples include training data derived from the output on one of the other analyses such as the quantitative analysis 70, the spectral analysis 75 and/or the statistical analysis 80.

The digitized data and/or the values of the properties of each entity or object 12 is securely encrypted, signed and packaged 112a for storage and/or transmission. As routine ultrasound monitoring in wearable devices has generally been excluded on cost grounds, little consideration has previously been given to security of the data transmitted from the monitoring ultrasonic devices 10 to the external processing system 15. However, the security, verifiability and immutability of such data and/or the values of the properties of each entity or object 12 can be critically important.

In an example of the present disclosure, the ultrasound system 5 uses key cryptography, hash functions, combining of the hash functions from previous data blocks and the combination of the data and/or the values of the properties of each entity or object 12 with metadata 110 allows the values and data to be securely, accountably and traceably transmitted and stored. Beneficially the data and/or the values of the properties of each entity or object 12 can be stored and/or transmitted in a form or variation of distributed ledger, such as Blockchain, DAG or the like. The incorporation of the data onto the distributed ledger maybe carried on the ultrasonic device 10 by the on-board processing system 35, on the external processing system 15 or distributed between both.

In the example, the data and/or the values of the properties of each entity or object 12 are key encrypted with one or both of a private key 100 associated with the object 12 that the ultrasonic device 10 is mounted to and/or a private key 105 associated with the ultrasonic device 10 itself. This encryption allows the data to be accessed only by a user responsible for the object (and who knows the object private key 100) and/or a user responsible for the ultrasonic device 10 (and who knows the device private key 105), even if the data is freely distributed. In this way, the access to the data and/or the values of the properties of each entity or object 12 can be distributed widely, including on $3^{rd}$ party servers, but be restricted to those with an interest in it. It also allows the source of the data and/or the values of the properties of each entity or object 12 to be verified, as only the holder of the appropriate private key can write the data and/or the values of the properties of each entity or object 12. Optionally, the data can be represented in the distributed ledger by a public key of the specific entity and/or the specific ultrasonic device 10.

The data and/or the values of the properties of each entity or object 12 generated by the ultrasonic device 10 is time-stamped such that the chronology is recorded. Optionally, the identify of the specific ultrasonic device 10 and/or the entity or object 12 is represented by a code, which is optionally the ultrasonic device 10 and/or entity or object's public key. In this way, the identity of the ultrasonic device 10 and/or entity or object can be kept secret, even if the data and/or the values of the properties of each entity or object 12 are shared widely throughout a network comprising $3^{rd}$ party computers.

The data and/or the values of the properties of each entity or object 12 is optionally stored and/or transmitted in block, such as blocks of a plurality of chronologically sequential values of the data and/or properties of each entity or object 12. Each entry in the block may represent a datum or determined property for a particular time, encoded with the timestamp. The block could, optionally comprise a fixed number of entries, i.e. of data and/or the values of the properties of each entity or object 12. The block optionally also comprises measurement metadata 110 relating to the measurements, e.g. to the specific, individual ultrasonic transducer 10 and/or the entity or object 12. The block may contain hashes of the data and/or properties of each entity or object 12 and/or the metadata. Beneficially, each block may comprise a hash of a previous block, e.g. sequentially previous block. In this way, any attempt to tamper with the data stored in a block will require the de-hashing and tempering with every preceding block. The hashes can be generated using any suitable cryptographic hashing functions such as, but not limited to, secure hashing algorithm 256 (SHA256). The hash function optionally generates a hash of a fixed length, regardless of the size of input.

Optionally the block or the constituent data and/or properties of each entity or object 12 comprised in the block may comprise an indication of the destination external processing system 15, which may be a public encryption key of the external processing system 15. In this way, block may also contain hashes of the data and/or properties of each entity or object 12 can be specifically addressed to specific external processing systems 15 in a way that only the intended external processing system 15 can access the data by using its private encryption key. This allows the blocks of data and/or properties of each entity or object 12 to be shared over a network but the contents of the data and/or properties of each entity or object 12 can only be read by users having the appropriate private encryption key.

The blocks may be stored in the distributed ledger. It will also be appreciated that the blocks could be formed by the on-board processing system 35, the external processing system 15 or distributed between the two.

Figure 6:
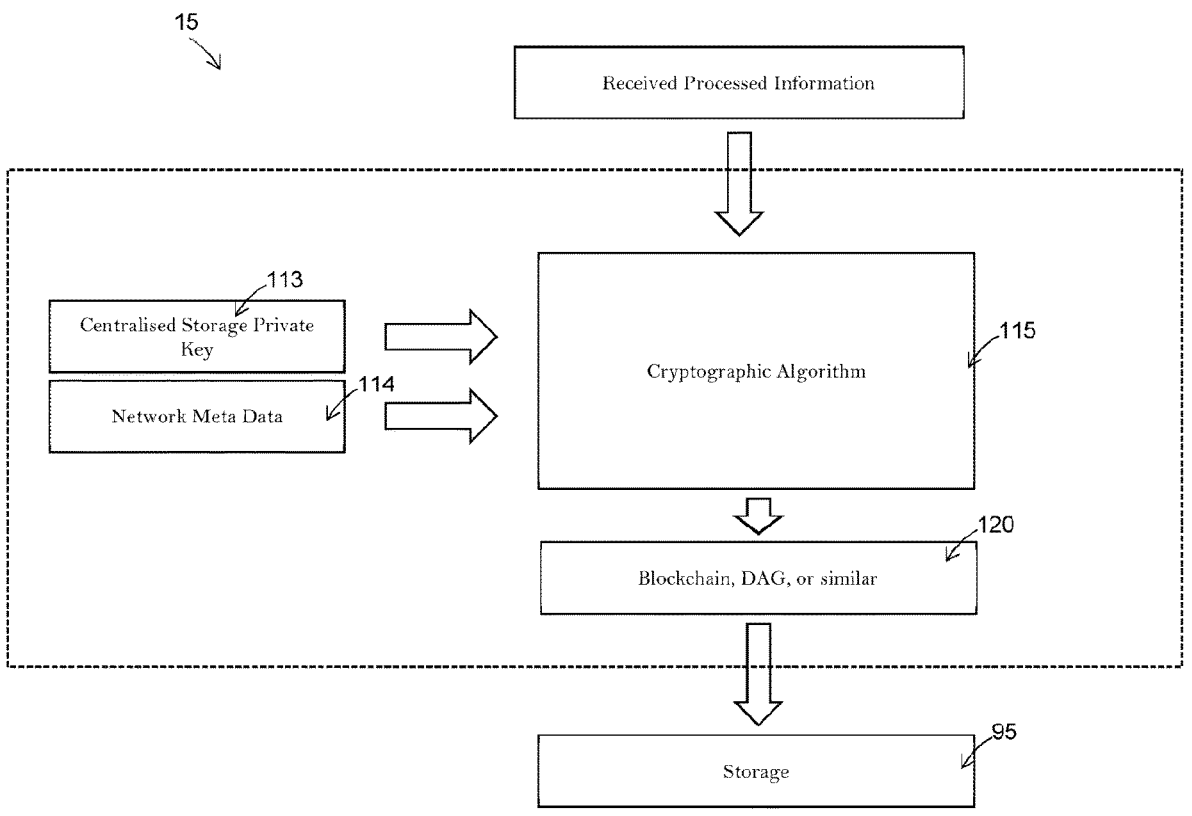
FIG. 6 is a detailed schematic further showing the flow of data shown in FIG. 4 that is performed on an external processing system.

FIG. 6 shows operations performed by the external processing system 15. The encrypted data and/or properties of each entity or object 12 from one or more of the ultrasonic devices are received by wireless communications and/or over a network or internet by the external processing system 15. The external processing system has access to its private key 113 and network meta data 114 that compliments the device meta data transmitted with the data and/or properties of each entity or object 12. These can be used in combination to further encrypt 115 the data and/or properties of each entity or object 12. Thereafter, the external processing system 15 adds the further encrypted received data and/or properties of each entity or object 12 to the distributed ledger 120, such as a blockchain or a directed acyclic graph or the like. The distributed ledger is stored in the centralized storage 95 or distributed to a network of storage, e.g. a distributed verification network.

The above detailed description of the drawings is provided in order to give an example of how the concepts described herein may be implemented. However, the scope of protection is defined by the claims and alternatives to the specific examples provided above would be apparent to a person skilled in the art and falling within the scope of the claims are intended to fall within the scope of the present disclosure. For example, although a distributed ledger such as blockchain, replicated journal technology, hyperledger, directed acyclic graph (DAG) and/or the like may be used in the examples given above, it will be appreciated that alternatives or additional methods to these approaches could be used to protect the integrity of the ultrasonic data. For example, other techniques could be used in which one or more or each of: the ultrasonic data is shared over a peer-to-peer network in which the ledger is spread to several nodes of the peer-to-peer network for example to replicate and store identical copies of the ledger; and/or consensus algorithms are used e.g. to ensure replication across nodes; and/or encryption technologies are used; there is a lack of a central controlling authority; and/or the ledger updates itself independently, and/or the like, and these other techniques are intended to fall within the scope of distributed ledger used herein so long as a skilled person would reasonably consider them to do so. That is, new examples or variations of distributed ledgers may develop and these are intended to be covered by references to distributed ledger herein.

The invention claimed is:

1. An ultrasonic device comprising:
at least one ultrasonic transducer that is operable to receive an ultrasonic waveform signal and produce an analogue electrical waveform signal responsive to, and indicative of, the received ultrasonic waveform signal;
an on-board processing system for processing the electrical waveform signal to determine data therefrom, wherein the on-board processing system comprises a digitizer or is otherwise configured to digitize the electrical waveform signal indicative of the received ultrasonic waveform signal from the at least one ultrasonic transducer or values thereof, such that the data generated by the on-board processing system comprises the digitized version of the electrical waveform signals produced by the ultrasonic transducers; and
a communications system for communicating the data with an external processing system, wherein the on-board processing system is configured to:
group the data generated by the on-board processing system and/or the digitized version of the electrical signals produced by the ultrasonic transducers into blocks for transmission or storage, wherein each block comprises a number or predetermined amount of chronologically sequential data generated by the on-board processing system and/or a portion of the digitized version of the electrical waveform signals produced by the ultrasonic transducers;
encrypt the data for storage and/or transmission; and
store and/or transmit the encrypted data generated by the on-board processing system that comprises the digitized version of the electrical waveform signals produced by the ultrasonic transducers as part of a Blockchain, directed acyclic graph (DAG) or other distributed ledger.

2. The ultrasonic device of claim 1, wherein the ultrasonic device is a wearable device.

3. The ultrasonic device of claim 1, wherein the ultrasonic device comprise an imaging device for imaging the entity, a non-destructive testing device and/or a monitoring device for monitoring changes in the entity over time.

4. The ultrasonic device of claim 1, wherein the on-board processing system is configured to process the electrical signal or a digitized version of the electrical signal or one or more properties derived from the electrical signal by performing one or more of: quantitative analysis, spectral analysis, statistical analysis, application of machine learning or artificial intelligence techniques to determine the data.

5. The ultrasonic device of claim 1, wherein the on-board processing system is configured to process the electrical signal(s) generated by the at least one ultrasonic transducers by digitally processing of the digitized electrical signal or data derived therefrom.

6. The ultrasonic device of claim 1, wherein the on-board processing system is configured to verify any data before including it in a block, wherein the verification is a verification with one or more external computers from a decentralized network of computers.

7. The ultrasonic device of claim 1, wherein the on-board processing system is configured to encrypt and/or encode the data or blocks of data and/or generate a hash of at least the data in the block and a hash or the data of at least one preceding block before transmitting or storing the data or block.

8. The ultrasonic device of claim 5, wherein the on-board processing system is configured to digitally enhance the digitized electrical signal from the at least one ultrasonic transducer or values thereof and/or filter the digitized electrical signal from the at least one ultrasonic transducer or values thereof.

9. The ultrasonic device of claim 8, configured to filter to digitized electronic signal using matched filtering using a wideband linear or arbitrarily swept chirp signal in a determined or predetermined frequency range.

10. The ultrasonic device of claim 1, wherein the on-board processing system has access to measurement metadata and is configured to combine the data with the measurement metadata as part of the encryption of the data.

11. The ultrasonic device of claim 1, comprising a power source for powering the at least one ultrasonic transducer, the on-board processing system, the communications system, and/or the data storage, the power source comprising an electrochemical power storage device, an electrostatic storage device, an inductive or other wireless charging or power receiving system and/or a mechanical or kinetic power source.

12. The ultrasonic device of claim 1, wherein the ultrasonic transducer(s) are flexible ultrasonic transducers that comprise a layer of non-polymeric, polycrystalline piezoelectric material on a conductive, flexible substrate.

13. The ultrasonic device of claim 12, wherein the layer of piezoelectric material has a thickness in the range of 2 to 20 μm, and the layer of piezoelectric material has a thickness that is half that of the substrate or less.

14. The ultrasonic device of claim 1, wherein the ultrasonic transducer(s) have a bandwidth that is greater than 100%, with a centre of frequency of the bandwidth being greater than 10 MHz.

15. The ultrasonic device of claim 1, configured for mounting or fixing to, or being in an item worn by, a living entity.

16. The ultrasonic device of claim 1, wherein the data determined by the on-board processing system comprises an indication or measure of a health or physiological condition such as pneumonia, chest infection, dehydration, muscle damage, skin damage, digestive health issues, cardiac dysfunction, or other suitable health, dental or physiological condition or complaint; or the data determined by the on-board processing system comprises an indication or measure of a condition, state or one or more properties of the entity.

17. A system comprising one or more ultrasonic devices and an external processing system, wherein the one or more ultrasonic devices comprise:
at least one ultrasonic transducer that is operable to receive an ultrasonic signal and produce an electrical signal responsive to, and indicative of, the received ultrasonic signal;
an on-board processing system for processing the electrical signal to determine data therefrom; and
a communications system for communicating the data with an external processing system,
wherein the ultrasonic device is configured to protect the integrity of the ultrasonic data using a distributed ledger; and
wherein the ultrasonic device(s) are configured to:
group the data generated by the on-board processing system and/or the digitized version of the electrical signals produced by the ultrasonic transducers into blocks for transmission or storage, wherein each block comprises a number or predetermined amount of chronologically sequential data generated by the on-board processing system and/or a portion of the digitized version of the electrical waveform signals produced by the ultrasonic transducers;

encrypt the data for storage and/or transmission; and store and transmit the encrypted data generated by the on-board processing system, including an encrypted digitized version of the electrical signals produced by the ultrasonic transducers, as part of a Blockchain, directed acyclic graph (DAG) or other distributed ledger, and communicate the encrypted ultrasonic data with the external processing system using the communications system of the respective ultrasonic device.

18. A method of determining and/or monitoring properties of an entity using at least one ultrasonic device, the one or more ultrasonic devices comprising:

at least one ultrasonic transducer that is operable to receive an ultrasonic signal and produce an electrical signal responsive to, and indicative of, the received ultrasonic signal;

an on-board processing system for processing the electrical signal to determine data therefrom, wherein the on-board processing system comprises a digitizer or is otherwise configured to digitize the electrical waveform signal indicative of the received ultrasonic waveform signal from the at least one ultrasonic transducer or values thereof, such that the data generated by the on-board processing system comprises the digitized version of the electrical waveform signals produced by the ultrasonic transducers; and a communications system for communicating the data with an external processing system, wherein the on-board processing system is configured to:

group the data generated by the on-board processing system and/or the digitized version of the electrical signals produced by the ultrasonic transducers into blocks for transmission or storage, wherein each block comprises a number or predetermined amount of chronologically sequential data generated by the on-board processing system and/or a portion of the digitized version of the electrical waveform signals produced by the ultrasonic transducers;

encrypt the data for storage and/or transmission; and store and/or transmit the encrypted data generated by the on-board processing system that comprises the digitized version of the electrical waveform signals produced by the ultrasonic transducers as part of a Blockchain, directed acyclic graph (DAG) or other distributed ledger;

the method comprising:

emitting an ultrasonic signal from the ultrasonic device into or onto the entity;

receiving an ultrasonic signal using the ultrasonic device, wherein the received signal comprises or is derived from the signal emitted into or onto the entity; determining ultrasonic data from the received signal; and protecting the integrity of the ultrasonic data using a distributed ledger.

19. The ultrasonic device of claim 12, wherein the substrate has a thickness in the range of 20 to 200 μm, and the layer of piezoelectric material has a thickness that is half that of the substrate or less.

* * * * *